United States Patent [19]

Pawloski et al.

[11] Patent Number: 4,510,101
[45] Date of Patent: Apr. 9, 1985

[54] HALOGENATED PHOSPHORUS HYDROXY-ALKYL AND T-ALKOXYALKYL ESTERS

[75] Inventors: Chester E. Pawloski, Bay City; Sally P. Ginter, Sanford, both of Mich.

[73] Assignee: The Dow Chemical Company, Midland, Mich.

[21] Appl. No.: 476,662

[22] Filed: Mar. 18, 1983

[51] Int. Cl.³ .................... C07F 9/11; C07F 9/32; C08G 18/00
[52] U.S. Cl. .................... 260/928; 260/930; 528/51
[58] Field of Search .................... 260/928, 930

[56] References Cited

U.S. PATENT DOCUMENTS 3,099,676 7/1963 Lanham .................... 260/928
3,192,242 6/1965 Birum .................... 260/928
3,423,486 1/1969 Ratz et al. .................... 260/928

*Primary Examiner*—Anton H. Sutto
*Attorney, Agent, or Firm*—Norman L. Sims

[57] ABSTRACT

The invention is phosphorus compounds containing α-halo hydroxyalkyl or α-halo t-alkoxyalkyl groups corresponding to the formula

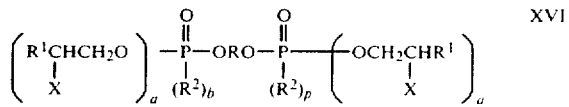

wherein
R independently in each occurrence is alkylene, haloalkylene, alkenylene, haloalkenylene, phenylene, diphenylene, halophenylene, dihalophenylene, and oxyalkylene;
$R^1$ independently in each occurrence is hydrogen, $CH_2OR^3$, $CH_2OH$, haloalkyl, phenyl, halophenyl or methyl phenoxy;
$R^2$ independently in each occurrence is haloalkyl, phenyl, haloaryl or alkyl;
$R^3$ independently in each occurrence is t-alkyl;
X independently in each occurrence is bromine or chlorine;
a is independently in each occurrence 1 or 2; and
b is independently in each occurrence 0 or 1,
with the proviso that at least one $R^1$ is $CH_2OR^3$ or $CH_2OH$.

8 Claims, No Drawings

HALOGENATED PHOSPHORUS HYDROXY-ALKYL AND T-ALKOXYALKYL ESTERS

BACKGROUND OF THE INVENTION

The invention relates to halogenated phosphorus esters which contain hydroxyalkyl and t-alkoxyalkyl groups. The compounds of this invention are useful as flame retardants, or intermediates in the preparation of flame retardants, for polyurethanes.

Polyurethanes, particularly polyurethane foam plastics, find widespread uses in industry for a plurality of purposes, and they are still gaining increasing interest. Because of their excellent heat and sound-absorbing properties, polyurethane foam plastics are widely used for example, in the building industry, as heat insulator in refrigerators and cars, pipelines, tanks, tank cars, and for a plurality of further purposes. A particularly beneficial effect which polyurethanes offer is the ease with which they can be produced on the spot. Polyurethane soft plastics are widely employed in commercial quantities for the manufacture of mattresses, upholstery for furniture and automobile seats, and for many other uses.

To be suitable for these uses, it is often necessary or at least desirable for the polyurethanes to have satisfactory flame retarding properties. Various attempts have already been made to render polyurethanes flame retardant. One involves adding a phosphorus-containing flame retarding agent thereto. In those cases, however, in which these additives are merely incorporated with the plastics, they are likely to migrate or become extracted therefrom, under outdoor conditions, especially if polyurethane foam plastics are concerned. A substantial progress in flame retarding polyurethanes has been achieved through the use of phosphorus-containing polyols, which are chemically bound in polyurethanes. These polyols can be made, for example, by the additive combination of epoxides with an acid of phosphorus, or its acid esters. Phosphorus compounds having additional halogen therein are known to improve the noninflammability of plastics as the use of phosphorus together with a halogen, which preferably is chlorine or bromine, has been found to produce a synergistic flame retarding effect.

It is commonly known that polyurethanes are produced by preparing a blend from high molecular weight compounds containing at least 2 active hydrogen atoms, and polyisocyanates in the presence of one or more catalysts and, if desired, expanding agents, surface-active substances and further auxiliaries. The compounds of high molecular weight include, for example, phosphorus- and halogen-containing polyols, which may be used alone or in combination with further customary compounds, such as polyetherpolyols, polyesterpolyols and polyester amides.

Phosphorus hydroxyalkyl esters are known in the art.

Baranauckas et al., U.S. Pat. No. 3,737,397, disclose esters of phosphonic acid containing three or more hydroxy groups, methods for the preparation thereof, and polyurethane foams having such compounds incorporated therein.

Vollmer et al., U.S. Pat. No. 3,978,170, disclose the production of polyols containing halogen and phosphorus. The polyols find use as flame retarding agents in plastics, particularly in polyurethane foams.

Wortmann et al., U.S. Pat. No. 3,850,859, disclose difficultly inflammable polyurethane foam plastics, and a process for making them with the use inter alia of a phosphorus- and chlorine-containing polyol as a flame-proofing component. The reference discloses processes for the preparation of phosphorus- and chlorine-containing polyols.

Albright, U.S. Pat. No. 4,133,846, discloses esters of pentavalent phosphorus acid and plastic compositions containing these esters as flame retardants. These esters contain halogen atoms and hydroxyl moieties.

Halogenated phosphorus compounds from which primary hydroxyl groups containing halogenated phosphorus compounds can be prepared in a controlled manner without the formation of undesirable by-products are needed. Halogenated phosphorus compounds which contain one or more reactive hydroxyl groups which have relatively high amounts of halogen incorporated therein are further needed.

SUMMARY OF THE INVENTION

The invention involves novel phosphorus compounds containing α-halo hydroxyalkyl or α-halo t-alkoxyalkyl groups corresponding to the formula

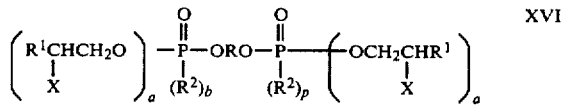

wherein
R independently in each occurrence is alkylene, haloalkylene, alkenylene, haloalkenylene, phenylene, diphenylene, halophenylene, dihalophenylene, and oxyalkylene;
$R^1$ independently in each occurrence is hydrogen, $CH_2OR^3$, $CH_2OH$, haloalkyl, phenyl, halophenyl or methyl phenoxy;
$R^2$ independently in each occurrence is haloalkyl, phenyl, haloaryl or alkyl;
$R^3$ independently in each occurrence is t-alkyl;
X independently in each occurrence is bromine or chlorine;
a is independently in each occurrence 1 or 2; and
b is independently in each occurrence 0 or 1, with the proviso that at least one $R^1$ is $CH_2OR^3$ or $CH_2OH$.

Another aspect of this invention is a polyurethane composition into which a flame retardant amount of the α-halo hydroxyalkyl phosphorus compounds has been incorporated. A further aspect of this invention is a method of preparing a flame retardant polyurethane by incorporating the α-halo hydroxyalkyl-containing phosphorus compounds of this invention into the backbone of the polyurethane resin.

The α-halo t-alkoxyalkylphosphorus compounds described herein are useful as intermediates in the preparation of α-halo hydroxyalkylphosphorus compounds without the formation of the troublesome by-products which are a problem in the prior art processes. The α-halo hydroxyalkylphosphorus compounds are useful as flame retardants in polyurethanes.

One novel feature of Applicants' invention is that the hydroxyl and t-alkoxy groups have a halogen on the adjacent carbon. This increases the flame retardancy of the compounds.

A surprising feature of this invention is that Applicants' compounds can be prepared in relatively pure form without significant formation of troublesome by-products.

DETAILED DESCRIPTION OF THE INVENTION

Herein alkylene, haloalkylene, alkenylene, haloalkenylene and oxyalkylene refer to straight and branched bivalent hydrocarbon chains in which the branches are alkyl or haloalkyl.

R is preferably alkylene, haloalkylene, alkenylene, haloalkenylene or oxyalkylene. R is most preferably $C_{1-10}$ alkylene, $C_{1-10}$ haloalkylene, $C_{1-10}$ alkenylene, $C_{1-10}$ haloalkenylene or $C_{1-10}$ oxyalkylene.

$R^1$ is preferably $CH_2OH$, $CH_2OR^3$ or haloalkyl, more preferably $CH_2OH$ and $CH_2OR^3$, and most preferably $CH_2OH$. $CH_2OH$ is most preferred as this group gives the novel compounds claimed reactive primary hydroxyl groups which will react with isocyanate compounds in a manner such that the novel α-halo hydroxyalkyl-containing phosphorus compounds are incorporated in the polyurethane backbone. $CH_2OR^3$ is a preferred embodiment because this substituent allows the formation of the desired novel α-halo hydroxyalkyl-containing phosphorus compounds in pure form, because there are no reactive hydroxyl groups to react with the phosphorus and the substituent can later be dealkylated to prepare the desired hydroxyl-containing compound. $R^3$ is preferably lower t-alkyl and most preferably t-butyl.

The above description of the claimed compounds includes the proviso that at least one $R^1$ is $CH_2OH$ or $CH_2OR^3$. At least one of these groups is necessary to allow the incorporation of the compounds into the backbone of a polyurethane or to allow the preparation of compounds which can be so incorporated. It is preferable that at least two R's be $CH_2OH$ or $CH_2OR^3$ so that the novel compounds are more readily incorporated into the polyurethane backbone or that such compounds can be readily prepared. It is most preferable that at least two R's are $CH_2OH$.

In the formula, a is preferably 2 and b is preferably 0. The novel compounds of this type are known as phosphorates.

The novel compounds of this invention can be prepared by several methods. In one method, two moles of a phosphite corresponding to the formula

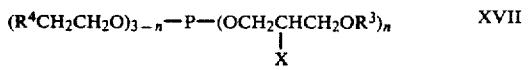   XVII are contacted with one mole of a dihydroxy compound corresponding to the formula

HOROH   XVIII in the presence of an alkali metal alkoxide catalyst under such conditions that the dihydroxy compound reacts with two of the phosphite compounds. This reaction is described by the equation below.

Equation IV

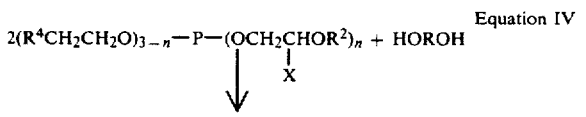

$2R^4CH_2CH_2OH$.

In the above equation R, $R^2$ and X are as defined above; n is 1 to 3; and $R^4$ is halogen, alkyl, haloalkyl, hydrogen, phenyl, halophenyl or methyl phenoxy.

The phosphite which is used above is prepared by methods well-known in the art. For example, $PCl_3$ is reacted with one or more suitable epoxides, provided $PCl_3$ is reacted with at least one mole of a dealkylatable epoxide. A dealkylatable epoxide is an epoxide which is substituted with a t-alkoxy group, for example, t-butyl glycidyl ether.

Suitable non-dealkylatable epoxides which can be used in conjunction with the dealkylatable epoxide include ethylene oxide, propylene oxide, butylene oxide, epichlorohydrin and the like. The more reactive epoxides react readily in the absence of a catalyst at suitable temperatures. In some cases, a catalyst may be necessary. Suitable catalysts are known in the art, and include halogenated titanium or zirconium compounds. A preferred catalyst is $TiCl_4$. Desirable temperatures include between about 0° C. and 50° C., preferably between about 20° C. and 40° C. Solvents can be used in this reaction. Suitable solvents include aromatic hydrocarbons such as toluene, and chlorinated hydrocarbons such as methylene chloride. When more than one epoxide is added, they can be added concurrently or sequentially. Sequential addition is preferred.

The by-product is a low-boiling compound which is removed during the process by distillation. Suitable conditions include elevated temperatures, preferably between about 100° C. and 150° C. The use of reduced pressure is advantageous, in that the removal of the low-boiling by-product is aided. When the evolution of the low-boiling by-product ceases, the reaction is complete.

The products are the t-alkoxylated species of the invention. These compounds can be dealkylated to prepare the primary hydroxyl-containing compounds of this invention. The dealkylation can be done by exposing the compounds prepared above to strong acids or an ion-exchange resin in the acid form at elevated temperatures. Desirable elevated temperatures are above 60° C., most preferably between about 100° C. and 120° C. Examples of strong acids include p-toluene sulfonic acid, phosphoric acid and the like.

In another method, two moles of $PCl_3$ are reacted with an alcohol corresponding to the formula $R-(OH)_4$   IXX at elevated temperatures. This reaction is described by the following equation:

Equation V

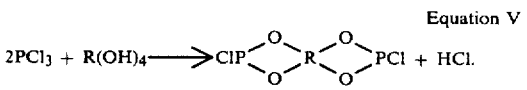

It is usually advantageous to use an excess of $PCl_3$. HCl and excess $PCl_3$ are by-products of the reaction and are removed by distillation after the reaction is completed. Suitable temperatures are between about 60° C. and 100° C., preferably between about 80° C. and 90° C. The product is a cyclic bis phosphite.

The reaction mixture is then cooled, and a chlorinated hydrocarbon solvent is added. Thereafter, two moles of bromine are added under conditions such that the reaction temperature is between about 25° C. and 30° C. The temperature is controlled by cooling or controlling the rate of addition. After addition of the bromine is complete, the reaction mixture is stirred for a period of time keeping the temperature between about 20° C. and 40° C. This reaction is illustrated by the following equation:

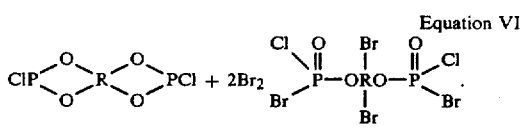

Equation VI

The product is a phosphorate.

This product is reacted with one or more epoxides such that the halogen atoms on the phosphorus are replaced with the group

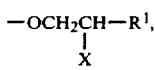

$-OCH_2CH-R^1$,
$\quad\quad\quad\ \ |$
$\quad\quad\quad\ \ X$ provided at least one mole of the epoxides are dealkylatable. Other suitable epoxides include those described above. Conditions for such addition are also as described above.

Another suitable method for the preparation of these compounds involves reacting

with one or more epoxides provided at least one of the epoxides is dealkylatable. This reaction can be done in the manner described above. The product is a phosphorate of the formula

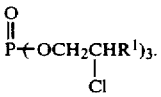     XX

Two moles of this phosphorate are then contacted with a dihydroxy compound HOROH at reflux for about 4 hours to about 8 hours. During this time, low-boiling hydrocarbon by-products which evolve, are removed. When the evolution ceases, the reaction is complete. The product is a phosphorate corresponding to the formula

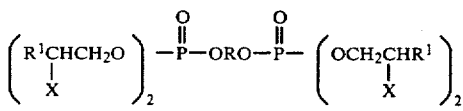     XXI wherein at least one $R^1$ is a $-CH_2OR^3$ group

The $-CH_2OR^3$ group can thereafter be dealkylated in the manner described above to prepare the primary hydroxy analogs.

Phosphonates may be prepared by the following method. A compound corresponding to the formula

     XXII is reacted with one mole of a dealkylatable epoxide, such as t-butyl glycidyl ether, in the manner described above. Two moles of the product are then contacted with one mole of a dihydroxy compound corresponding to the formula $R(OH)_2$. The product corresponds to the formula

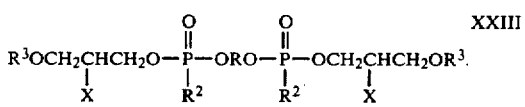     XXIII

Such compounds can be dealkylated in the manner described above to prepare the dihydroxy analogs.

The above-described methods for the preparation of the claimed compounds are merely illustrative. Other methods of preparation are described in the examples below.

The compounds of this invention which contain primary hydroxyl groups may be readily reacted with organic polyisocyanate alone or in combination with other reactants used in the fabrication of polyurethane polymers. Persons of ordinary skill in the art are well able to devise suitable formulations for producing polyurethanes according to this invention. Descriptions of the various reactants for such formulations are found in the following publications the teachings of which are incorporated herein by reference: *Kirk-Othmer Encyclopedia of Chemical Technology*, "Foamed Plastics", Vol. 9, pp. 853–854 (1966) and Saunders et al., *Polyurethanes*, Chemistry and Technology, Vols. I and II, Interscience Publishers 1963.

The polyurethanes of this invention comprise organic polyisocyanates, polyahls and flame retardant amounts of the α-halo hydroxyalkyl phosphorus compounds of this invention. Alternatively, the α-halo hydroxyalkyl phosphorus compounds of this invention may be the polyahls polymerized with the organic polyisocyanates to prepare polyurethanes.

Any amount of the α-halo hydroxyalkyl phosphorus which is flame retardant is suitable for this invention. Preferably, flame retardant amounts of α-halo hydroxyalkyl phosphorus compounds are between about 5 and 100 parts by weight of the polyahl, most preferably between about 10 and 50 parts by weight of the polyahl.

Any of the aforementioned phosphorus compounds containing α-halo hydroxyalkyl groups and optionally a polyahl is readily reacted with an organic polyisocyanate to form desired polyurethane products using conventional polyurethane reaction conditions and procedures. Such reaction and procedures are optionally carried out in the presence of chain extending agents, catalysts, surface active agents, stabilizers, blowing agents, fillers and/or pigments. In the preparation of foamed polyurethane, suitable procedures for the preparation of same are disclosed in U.S. Pat. No. 24,514, which is incorporated herein by reference. When water is added as the blowing agent, corresponding quantities of excess isocyanate to react with the water and produce carbon dioxide may be used. It is also possible to proceed with the preparation of the polyurethane plastics by a prepolymer technique wherein an excess of organic polyisocyanate is reacted in a first step with the phosphorus compounds containing α-halo hydroxyalkyl groups and optionally a polyol of the present invention to prepare a prepolymer having free isocyanate groups which is then reacted in a second step with water to prepare a foam. Alternatively, the components may be reacted in a single working step commonly known as the "one-shot" technique of preparing polyurethanes. Furthermore, instead of water, low boiling hydrocarbons such as pentane, hexane, heptane, pentene, and heptene; azo compounds such as azohexahydrobenzodinitrile; halogenated hydrocarbons such as dichlorodifluoromethane, trichlorofluoromethane, dichlorodifluoroethane, vinylidene chloride and methylene chloride may be used as blowing agents.

The foams may also be prepared by the froth technique as described in U.S. Pat. Nos. 3,755,212; 3,849,156 and 3,821,130 which are also incorporated herein by reference.

Organic polyisocyanates which may be employed include aromatic, aliphatic and cycloaliphatic polyisocyanates and combinations thereof. Representative of these types are the diisocyanates such as m-phenylene diisocyanate, tolylene-2,4-diisocyanate, tolylene-2,6-diisocyanate, hexamethylene-1,6-diisocyanate, tetramethylene-1,4-diisocyanate, cyclohexane-1,4-diisocyanate, hexahydrotolylene diisocyanate (and isomers), naphthylene-1,5-diisocyanate, 1-methoxyphenyl-2,4-diisocyanate, diphenylmethane-4,4-diisocyanate, 4,4'-biphenylene diisocyanate, 3,3'-dimethoxy-4,4'-biphenyl diisocyanate, 3,3'-dimethyl-4,4'-biphenyl diisocyanate, and 3,3'-dimethyldiphenylmethane-4,4'-diisocyanate; the triisocyanates such as 4,4',4''-triphenylmethane triisocyanate, polymethylene polyphenylisocyanate and tolylene-2,4,6-triisocyanate; and the tetraisocyanates such as 4,4'-dimethyldiphenylmethane-2,2',5,5'-tetraisocyanate. Especially useful due to their availability and properties are tolylene diisocyanate, diphenylmethane-4,4'-diisocyanate and polymethylene polyphenylisocyanate.

Crude polyisocyanate may also be used in the practice of the present invention, such as crude toluene diisocyanate obtained by the phosgenation of a mixture of toluene diamines or crude diphenylmethylene diisocyanate obtained by the phosgenation of crude diphenylmethylenediamine. The preferred undistilled or crude isocyanates are disclosed in U.S. Pat. No. 3,215,652.

The term polyahl includes any organic compound having at least two active hydrogen moieties and an average molecular weight of at least 62. For the purpose of this invention, an active hydrogen moiety refers to a moiety containing a hydrogen atom which, because of its position in the molecule, displays significant activity according to the Zerewitnoff test described by Woller in the *Journal of The American Chemical Society*, Vol. 49, p. 3181 (1927). Illustrative of such active hydrogen moieties are —COOH, —OH, NH$_2$, =NH, CONH$_2$, SH and —CONH—. Typical polyahls include polyols, polyamines, polyamides, polymercaptans, polyacids and the like, particularly as exemplified in U.S. Pat. No. 3,928,299 incorporated herein by reference.

Of the foregoing polyahls, the polyols are preferred. Examples of such polyols useful in this invention are the polyol polyethers, the polyol polyesters, hydroxy functional acrylic polymers, hydroxyl-containing epoxy resins, polyhydroxy terminated polyurethane polymers, polyhydroxyl-containing phosphorus compounds and alkylene oxide adducts of polyhydric thioethers including polythioethers, acetals including polyacetals, aliphatic and aromatic polyols and thiols including polythiols, ammonia and amines including aromatic, aliphatic and heterocyclic amines including polyamines as well as mixtures thereof. Alkylene oxide adducts of compounds which contain two or more different groups within the above-defined classes may also be used such as amino alcohols which contain an amino group and a hydroxyl group. Also alkylene adducts of compounds which contain one —SH group and one —OH group as well as those which contain an amino group and a —SH group may be used.

Polyether polyols which are most advantageously employed in the practice of this invention are the polyalkylene polyether polyols including the polymerization products of alkylene oxides and other oxiranes with water or polyhydric alcohols having from two to eight hydroxyl groups. Exemplary alcohols that are advantageously employed in making the polyether polyol include ethylene glycol, 1,3-propylene glycol, 1,2-propylene glycol, 1,4-butylene glycol, 1,3-butylene glycol, 1,2-butylene glycol, 1,5-pentanediol, 1,7-heptanediol, glycerol, 1,1,1-trimethylolpropane, 1,1,1-trimethylolethane, hexane-1,2,6-triol, α-methyl glucoside, pentaerythritol, erythritol, pentatols and hexatols. Also included within the term "polyhydric alcohol" are sugars such as glucose, sucrose, fructose and maltose as well as compounds derived from phenols such as 2,2-(4,4'-hydroxyphenyl)propane, commonly known as bisphenol A. Illustrative oxiranes that are advantageously employed in the preparation of the polyether polyol include simple alkylene oxides such as ethylene oxide, propylene oxide, butylene oxide, and amylene oxide; glydicyl ethers such as t-butyl glycidyl ether and phenyl glycidyl ether; and random or block copolymers of two or more of these oxiranes. The polyalkylene polyether polyols may be prepared from other starting materials such as tetrahydrofuran and alkylene oxide tetrahydrofuran copolymers; epihalohydrins such as epichlorohydrin; as well as aralkylene oxides such as styrene oxide. The polyalkylene polyether polyols may have primary, secondary or tertiary hydroxyl groups and, preferably, are polyethers prepared from alkylene oxides having from two to six carbon atoms such as ethylene oxide, propylene oxide and butylene oxide. The polyalkylene polyether polyols may be prepared by any known process such as, for example, the process disclosed in *Encyclopedia of Chemical Technology*, Vol. 7, pp. 257–262, published by Interscience Publishers, Inc. (1951), or in U.S. Pat. No. 1,922,459. Also suitable are polyether polyols and processes for preparing them that are described in Shick, M. J., *Nonionic Surfactants*, Marcel Dekker, Inc., New York (1967), U.S. Pat. Nos. 2,891,073; 3,058,921; 2,871,219 and British Pat. No. 898,306. Polyether polyols which are most preferred include the alkylene oxide addition products of water, trimethylolpropane, glycerine, pentaerythritol, sucrose, sorbitol, propylene glycol and blends thereof having hydroxy equivalent weights of from about 250 to about 5000.

The phosphorus compounds containing α-halo hydroxyalkyl groups of this invention are preferably employed in combination with other polyahls commonly employed in the art. Accordingly, any of the polyahls which are described above for use in the preparation of the polymer dispersions of the present invention may be employed.

Chain-extending agents which may be employed in the preparation of the polyurethane compositions of the present invention include those compounds having at least two functional groups bearing active hydrogen atoms such as water, hydrazine, primary and secondary diamines, amino alcohols, amino acids, hydroxy acids, glycols or mixtures thereof. A preferred group of chain-extending agents includes water and primary and secondary aromatic diamines which react more readily with the isocyanate than does water such as phenylenediamine, bis(3-chloro-4-aminophenyl)methane, 2,4-diamino-3,5-diethyl toluene, trisecondary butanolamine, isopropanolamine, diisopropanolamine, N-(2-hydroxypropyl)ethylenediamine, and N,N'-di(2-hydroxypropyl)ethylenediamine.

The urethane reaction of polyisocyanate with the phosphorus compounds containing α-halo hydroxyalkyl groups and optionally polyahls is advantageously carried out in the presence of an amount of a urethane-type catalyst which is effective to catalyze the reaction of the hydroxy group on the α-hydroxyalkyl group with the polyisocyanate. Preferably, the amount of urethane catalyst is an amount comparable to that used in conventional urethane-type reactions.

Any suitable urethane catalyst may be used including tertiary amines, such as, for example, triethylenediamine, N-methyl morpholine, N-ethyl morpholine, diethyl ethanolamine, N-coco morpholine, 1-methyl-4-dimethylaminoethyl piperazine, 3-methoxy-N-dimethylpropylamine, N,N-dimethyl-N',N'-methyl isopropyl propylene diamine, N,N-diethyl-3-diethylaminopropylamine, dimethyl benzylamine and the like. Other suitable catalysts are, for example, tin compounds such as stannous chloride, tin salts of carboxylic acids such as dibutyltin di-2-ethyl hexanoate, as well as other organometallic compounds such as are disclosed in U.S. Pat. No. 2,846,408.

A wetting agent(s) or surface-active agent(s) is generally necessary for production of high grade polyurethane foam according to the present invention, since in the absence of same, the foams collapse or contain very large uneven cells. Numerous wetting agents have been found satisfactory. Nonionic surfactants and wetting agents are preferred. Of these, the nonionic surface-active agents prepared by the sequential addition of propylene oxide and then ethylene oxide to propylene glycol and the solid or liquid organosilicones have been found particularly desirable. Other surface-active agents which are operative, although not preferred, include polyethylene glycol ethers of long chain alcohols, tertiary amine or alkylolamine salts of long chain alkyl acid sulfate esters, alkyl sulfonic esters and alkyl arylsulfonic acids.

SPECIFIC EMBODIMENTS

The following examples are included for illustrative purposes and do not limit the scope of the invention or claims. All percentages are by weight unless otherwise stated.

EXAMPLE 1

Preparation of PHOSPHORUS ACID:
P,P'-(2,3-dibromo-2-butene-1,4-diyl)
P,P'-bis(2-chloroethyl)
P,P'-bis(2-chloro-3-hydroxypropyl) ester Into a 500-ml flask equipped with a stirrer and distillation column are placed 120 g of O,O-di(2-chloroethyl)-O-(2-chloro-3-(1,1-dimethylethoxy)propyl) phosphite (0.34 mole) and 1 g of potassium t-butoxide. This mixture is stirred and slowly heated to 130° C. under reduced pressure until the desired amount of by-product, (2-chloroethanol), is collected. The mixture is allowed to cool to 100° C. and 10 g of a macroporous sulfonated styrene-divinylbenzene copolymer are added. The heating is continued at 100° C. until nuclear magnetic resonance spectra show dealkylation of the t-butoxy group is complete. Some tetrahydrofuran is added to aid in thinning the oil. The solids are removed and the resulting oil is stirred with 25 g of sodium carbonate. The mixture is again filtered and the low boilers distilled off under reduced pressure at 70° C. 94 g Of a thick oil is recovered. This is an 85 percent yield. The product has a molecular weight of 648, a viscosity of 664,000 and contains 23.4 percent bromine, 20.8 percent chlorine, 9.1 percent phosphorus and has two reactive hydroxyls.

EXAMPLE 2

Preparation of PHOSPHORIC ACID:
2,2-bis(bromomethyl)-1,3-propanediyl
bis(2-chloroethyl)bis(bromo-3-hydroxypropyl) ester Into a 2-liter flask equipped with a reflux condenser and dropping funnel are placed 68 g of pentaerythritol (0.5 mole) and 172 g of phosphorus trichloride (1.25 moles). This mixture is stirred and slowly heated to 80° C. When the reaction is complete, the excess phosphorus trichloride and HCl are distilled off under reduced pressure. The mixture is allowed to cool and 600 ml of carbon tetrachloride is added. The mixture is cooled in a cold-water bath while 160 g of bromine (1.0 mole) is added dropwise. The reaction temperature of 25° C.-30° C. is controlled by addition rate. The mixture is stirred for 30 minutes and 1 ml of TiCl$_4$ is added. t-Butyl glycidyl ether (t-BGE) (65 g, 0.5 mole) is added dropwise and the mixture stirred until reaction is complete. Another ml of TiCl$_4$ is added and 20 g of ethylene oxide (0.5 mole) is added dropwise. When this reaction is complete another 65 g of t-BGE is added (0.5 mole) and stirred until reaction is complete. Finally, another 40 g of ethylene oxide (0.5+ mole) is added dropwise and the mixture refluxed one hour. The flask is equipped with a short distillation column and low boilers removed at 50° C. to give 476 g of the intermediate as a thick oil. The dealkylation catalyst (5 g of 85 percent phosphoric acid) is added and distillation continued until 125° C. is obtained. Heating is continued at this temperature until dealkylation of the t-butoxy group is complete by nuclear magnetic resonance spectra. The product (406 g) is a dark thick oil, with a viscosity of 136,000 cps Brookfield at 25° C. This is a 99 percent yield. The product has a molecular weight of 821 and contains 39.0 percent bromine, 8.6 percent chlorine, 7.6 percent phosphorus and two reactive hydroxyls.

EXAMPLE 3

Preparation of PHOSPHORIC ACID:
P,P'-(2,2-bis(chloromethyl)-1,3-propanediyl)
P,P'-bis(2-chloroethyl)
P,P'-bis(2-chloro-3-hydroxypropyl) ester Into a 2-liter flask are placed 68 g pentaerythritol (0.5 mole) and 172 g phosphorus trichloride (1.0+ mole). The reactants are slowly heated to 80° C. When reaction is complete, the excess phosphorus trichloride and HCl are distilled out under reduced pressure. Carbon tetrachloride (300 ml) is added and the mixture cooled while 72 g of chlorine (1 mole) is bubbled into the reaction mixture. The reaction temperature is controlled below 50° C. After stirring 30 minutes, one ml of $TiCl_4$ is added followed by the addition of 65 g of t-BGE (0.5 mole), 20 g of ethylene oxide (0.5 mole), 65 g of t-BGE (0.5 mole) and 40 g of ethylene oxide (0.5+ mole) at 30-minute intervals between additions. After these additions, the reaction mixture is refluxed one hour and allowed to stand. The flask is equipped with a short distillation column and low boilers removed to 80° C. The catalyst (5 g of 85 percent phosphoric acid) is added and heating continued to 115° C. until dealkylation is complete. The product (325 g) is an oil, 55,000 cps Brookfield viscosity, 99 percent yield. The product has a molecular weight of 643 and contains 33.1 percent chlorine, 9.6 percent phosphorus and two reactive hydroxyls.

EXAMPLE 4

Preparation of 1,2-ETHYLENE: bis (O-(2-chloroethyl)-O-(2-chloro-3-hydroxypropyl)phosphorate)

$POCl_3$ (154 g, 1.0 mole), 400 ml of methylene chloride and 1 ml of $TiCl_4$ are stirred in a 500-ml flask and cooled in a cold-water bath while 44 g of ethylene oxide (1.0 mole) is added dropwise. After this addition, 130 g of t-butyl glycidyl ether (1.0 mole) is added dropwise. The reaction mixture is allowed to slowly warm to room temperature and is then refluxed for 2 hours until the epoxy test is passed. The ethylene glycol (35 g, 0.5 mole) is added dropwise. After this addition, the mixture is refluxed for 4 hours. The flask is equipped with a short distillation column and low boilers removed until 100° C. is obtained. The reaction is held at this temperature until dealkylation of the t-butoxy groups is complete by nuclear magnetic resonance spectra. The product (246 g) is a thick oil, 121,000 cps Brookfield viscosity, 93 percent yield. The product has a molecular weight of 532 and contains 26.7 percent chlorine, 11.6 percent phosphorus and two reactive hydroxyls.

EXAMPLE 5

Preparation of ETHYLENE:
1,2-(bis(0-(2-chloro-3-hydroxypropyl)-0-(2,3-dichloropropyl)phosphorate Phosphoryl chloride (154 g, 1.0 mole) and 400 ml of methylene chloride are stirred in a one-liter flask while 31 g of ethylene glycol (1.0 mole) is added dropwise. An exothermic reaction takes place. The mixture is purged with nitrogen for one hour with stirring. After the HCl ceases to evolve, one ml of $TiCl_4$ is added and a solution of 130 g of t-BGE (1.0 mole) and 93 g of epichlorohydrin is added dropwise. After this addition, the mixture is refluxed until the epoxy test is passed. Another 10 g of epichlorohydrin is added and the mixture is refluxed for one hour. The flask is equipped with a short distillation column and low boilers removed to 125° C. until dealkylation is complete by nuclear magnetic resonance spectra. The product (275 g) is a very thick oil with a viscosity of 2,760,000 cps, 88 percent yield. The product has a molecular weight of 629.0 and contains 33.9 percent chlorine, 9.9 percent phosphorus and two reactive hydroxyl groups.

EXAMPLE 6

Preparation of PROPYLENE:
2,2-bis(bromomethyl)-1,3-bisO,O-di(2-chloro-3-hydroxypropyl)phosphorate)

FR-1138 (71 g, 0.25 mole) (a mixture of brominated pentaerythritols with at least 80 percent $(HOCH_2)_2C(CH_2Br)_2$), 500 ml of methylene chloride and 55 g of sodium carbonate (0.50+ mole) are stirred in a one-liter flask while 207 g of O,O -(2-chloro-3-(1,1-dimethylethoxypropyl)chloridophosphorate) (0.5 mole) is added dropwise. There is no apparent exotherm. After this addition, the mixture is stirred at reflux for 8 hours. Solids are filtered off and the product phase is washed with 200 ml of water. The product layer is separated, dried over sodium sulfate, filtered and low boilers are distilled off to 80° C. The dealkylation catalyst (3 g of 85 percent phosphoric acid) is added and the mixture heated to 130° C. until the dealkylation of the t-butoxy group is complete by nuclear magnetic resonance spectra. The product (173 g) is a very thick oil with a viscosity of 520,000 cps, 87 percent yield. The product has a molecular weight of 792 and contains 20.2 percent bromine, 17.9 percent chlorine and 7.8 percent phosphorus with four reactive hydroxyls.

EXAMPLE 7

Preparation of 2-buten-1,4-diyl:
2,3-dibromo-bis(di-O,O-(2-chloro-3-hydroxypropyl)-phosphoro)

Into a one-liter flask are placed 190 g of O,O -di(2-chloro-3-(1,1-dimethylethoxy)propyl)phosphite (0.5 mole), 400 ml of carbon tetrachloride and 58 g of 2,3-dibromo-1,4-butenediol (0.25 mole). This mixture is stirred while 55 g of triethylamine (0.5+ mole) is added dropwise. An exothermic reaction takes place. During the remainder of the addition, the mixture is cooled in a cold-water bath. The mixture is stirred at reflux for 6 hours and allowed to stand. After cooling, 200 ml of water is added and the mixture stirred. The product layer is separated and washed again with 200 ml of water. The product layer is separated and dried over sodium sulfate. The solids are filtered off and low boilers removed to 100° C. over a short distillation column. The dealkylation catalyst (3 g of 85 percent phosphoric acid) is added and the mixture heated at 125° C. until dealkylation of the t-butoxy group is complete by nuclear magnetic resonance spectra. The product (181 g) is a thick oil and has a viscosity of 130,000 cps, 93 percent yield. The product has a molecular weight of 776.0 and contains 20.6 percent bromine, 18.3 percent chlorine and 8.0 percent phosphorus with four reactive hydroxyls.

EXAMPLE 8

Preparation of PROPYLENE:
2-chloro-1-(di(2-chloro-3-hydroxypropyl)phosphoro)-3-(di(2,3-dichloropropyl)phosphoro)

Into a one-liter flask is placed 103 g of O-(2-chloro-3-hydroxypropyl)-O,O-di(2,3-dichloropropyl)phosphorate (0.25 mole), 300 ml of methylene chloride and 26 g of triethylamine (0.25 mole). This mixture is stirred while 104 g of O,O-(di(2-chloro-3-)-1,1-dimethylethoxypropyl)chloridophosphorate (0.25 mole) is added dropwise. A slight exotherm takes place. This mixture is then stirred for one hour at room temperature and 2 hours at reflux. After cooling, 200 ml of water is added and the mixture stirred. The product layer is separated and washed again with 200 ml of dilute HCl solution, separated and dried over sodium sulfate, and then filtered and distilled until 130° C. is obtained. Dealkylation occurs without a catalyst. The mixture is heated until dealkylation is complete by nuclear magnetic resonance spectra. The product (147 g) is a thick oil which has a viscosity of 130,000 cps, 87 percent yield. The product has a molecular weight of 677.5 and contains 36.7 percent chlorine and 9.2 percent phosphorus with two reactive hydroxyls.

EXAMPLE 9

Preparation of ETHYLENE:
1,2-bis(O-(2-chloro-3-hydroxypropyl)chloromethylphosphono)

Chloromethylphosphonic dichloride (84 g, 0.5 mole), 400 ml of methylene chloride and 1 ml TiCl₄ are stirred in a one-liter flask while 65 g of t-BGE (0.5 mole) is added dropwise. An exotherm takes place. The mixture is than refluxed until the epoxy test is passed. The mixture is poured off and allowed to cool. Into the flask is placed 16 g of ethylene glycol (0.25 mole) and 55 g of sodium carbonate (0.5+ mole). This mixture is stirred with 100 ml of methylene chloride while the reaction product from the earlier reaction is added dropwise. The reaction is cooled in a cold-water bath during this addition since the reaction is exothermic. After this addition, the mixture is refluxed for 4 hours and allowed to cool. The solids are filtered off and the low boilers removed to 100° C. over a short distillation column. The dealkylation catalyst (4 g of 85 percent phosphoric acid) is added and heating continued at 130° C. until dealkylation of the t-butoxy group is complete by nuclear magnetic resonance spectra. The product (90 g) is a thick oil which has a viscosity of 151,000 cps, 80 percent yield. The product has a molecular weight of 472.0 and contains 30.1 percent chlorine and 13.1 percent phosphorus with two reactive hydroxyls.

EXAMPLE 10

Preparation of PHOSPHORIC ACID: 1,4-butanediyl bis(oxy-2-chloro-3,1-propanediyl) tetrakis(2-chloro-3-hydroxypropyl) ester O,O-di(2-chloro-3-(1,1-dimethylethoxy)propyl)-chloridophosphorate (207 g, 0.5 mole), 500 ml of methylene chloride (0.5 mole) and 1 ml of TiCl₄ are stirred in a one-liter flask while 51 g of 1,4-butane diglycidyl ether (0.25 mole) is added dropwise at reflux temperatures. After this addition, the mixture is refluxed until the reaction passes the epoxy test. The flask is equipped with a short distillation column and low boilers are distilled out to 80° C. The dealkylation catalyst (3 g of 85 percent phosphoric acid) is added and the mixture heated to 130° C. until dealkylation is complete by nuclear magnetic resonance spectra. The product (195 g) is a thick oil with a viscosity of 216,000 cps, 97 percent yield. The product has a molecular weight of 805.0 and contains 26.5 percent chlorine and 7.7 percent phosphorus with four reactive hydroxyls.

EXAMPLE 11-20

Preparation of polyurethanes containing α-halo hydroxyalkylphosphorus compounds

Procedure

Several polyurethanes, which contain one of the α-halo hydroxyalkylphosphorus compounds, are prepared in the following manner. An α-halo hydroxyalkyl phosphorus compound (hereinafter referred to as F.R. Polyol), is combined with a sucrose/glycerine initiated polypropylene oxide with a hydroxyl number of 490 (hereinafter referred to as Polyol 1), an aminoethylethanolamine initiated polypropylene oxide with a hydroxyl number of 800 (hereinafter referred to as Polyol 2), a stannous catalyst (commonly known and referred to hereinafter as T-131 ®, available from M&T Chemicals, Woodbridge Avenue, Rahway, N.J.), a dimethylcyclohexylamine catalyst (commonly known and referred to hereinafter as Polycat ® 8, available from Abbott Laboratories, Chicago, Ill.), Freon ® 11B (trichlorofluoromethane, available from E. I. du Pont de Nemours & Co., Wilmington, Del.), and a silicone surfactant (commonly known as DC-197 ®, available from Dow Corning Corp., Midland, Mich.). This mixture is referred to hereinafter as the B side. The B side is then combined with 4,4'-diphenylmethane diisocyanate (commonly known as Mondur ® MR, available from Mobay) (this compound is referred to hereinafter as the A side) with stirring to prepare a polyurethane foam. The cream time, string time and tack-free time are noted.

The polyurethanes produced by the method described above are then subjected to the vertical burn test. The vertical burn test involves ignition of a small foam strip of the polyurethane (⅜"×3"×¼") in a controlled oxygen atmosphere (25 percent O₂) and measurement of the time required for the foam to burn 2 inches. The burn rate is then calculated in inches per minute. It is believed that a vertical burn rate of less than 10 inches per minute for rigid polyurethane foam would enable the foam to pass the Class II flame spread requirement (less than or equal to 75 F.S.) for the ASTM E-84 (25-foot tunnel) test.

Table I below shows the amount of each component in the polyurethanes prepared. Table II shows the results of the vertical burn test, the density of the polyurethane foams, the percent of polyol and the Mondur ® MR Index. The Mondur ® MR Index gives the relative percentage of reactive isocyanate moieties in relation to the reactive hydroxyl moieties in the polyurethane.

TABLE I

| | Examples | | | | | | | | | |
|---|---|---|---|---|---|---|---|---|---|---|
| | 11 | 12 | 13 | 14 | 15 | 16 | 17 | 18 | 19 | 20 |
| Side B | | | | | | | | | | |

TABLE I-continued

|  | Examples | | | | | | | | | |
|---|---|---|---|---|---|---|---|---|---|---|
|  | 11 | 12 | 13 | 14 | 15 | 16 | 17 | 18 | 19 | 20 |
| F.R. Polyol Source (Example) | 1 | 2 | 3 | 4 | 5 | 6 | 7 | 8 | 9 | 10 |
| Amount (g) | 10 | 15 | 10 | 15 | 10 | 14.3 | 10 | 17.9 | 10 | 16.7 |
| Polyol 1 (g) | 90* | 85* | 90* | 85* | 90* | 67.7 | 90* | 64.1 | 90 | 65.3 |
| Polyol 2 (g) |  |  |  |  |  | 18.0 |  | 18.0 |  | 16.7 |
| T-131 ® (g) | 0.2 | 0.2 | 0.2 | 0.2 | 0.2 | 0.2 | 0.2 | 0.2 | 0.3 | 0.2 |
| Polycat ® (g) | 1.0 | 1.0 | 1.0 | 1.0 | 1.0 | 1.0 | 1.0 | 1.0 | 1.0 | 1.0 |
| DC-197 ® | 2.0 | 2.0 | 2.0 | 2.0 | 2.0 | 2.0 | 2.0 | 2.0 | 2.0 | 2.0 |
| Freon ® 11B | 56 | 54.4 | 56.1 | 56.2 | 48.9 | 49.5 | 49.5 | 48.9 | 53.3 | 49.5 |
| Side A |  |  |  |  |  |  |  |  |  |  |
| Mondur ® MR | 180.4 | 172.2 | 180.8 | 176.1 | 144.8 | 147.8 | 147.9 | 144.5 | 166.6 | 147.6 |

*The Polyol is an 80:20 mixture of Polyol 1 and Polyol 2.

TABLE II

|  | Examples | | | | | | | | | |
|---|---|---|---|---|---|---|---|---|---|---|
|  | 11 | 12 | 13 | 14 | 15 | 16 | 17 | 18 | 19 | 20 |
| Cream Time (sec) | 14 | 20 | 22 | 11 | 14 | 20 | 18 | 18 | 25 | 16 |
| String Time (sec) | 25 | 46 | 55 | 32 | 34 | 52 | 55 | 42 | 110 | 45 |
| Tack-free Time (sec) | 40 | 68 | 83 | 49 | 50 | 90 | 87 | 65 | 205 | 60 |
| % Polyol* | 10 | 10 | 10 | 15 | 10 | 10 | — | 10 | 10 | 10 |
| Density (lb/ft$^3$) | 2.4 | 2.1 | 1.9 | 2.4 | 1.7 | 1.7 | 1.7 | 1.8 | 1.7 | 1.6 |
| Mondur ® MR Index | 150 | 150 | 150 | 150 | 120 | 120 | 120 | 120 | 120 | 120 |
| Vertical Burn (in/min) | 6.6 | 5.6 | 5.8 | 5.2 | 8.4 | 8.0 | — | 8.0 | 7.8 | 8.6 |

*% Polyol is the percentage of the F.R. Polyol in the polyol mixture used to prepare the polyurethanes.

Table II demonstrates that the polyurethane foams prepared containing the halogenated phosphorus hydroxyalkyl esters have good flame retardant properties.

What is claimed is:

1. Phosphorus compounds containing α-halo hydroxyalkyl or α-halo t-alkoxyalkyl groups corresponding to the formula

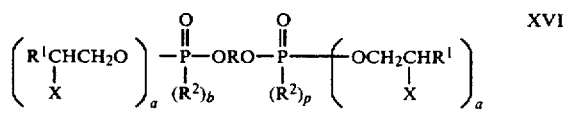

XVI wherein
R independently in each occurrence is alkylene, haloalkylene, alkenylene, haloalkenylene, phenylene, diphenylene, halophenylene, dihalophenylene, and oxyalkylene;
$R^1$ independently in each occurrence is hydrogen, $CH_2OR^3$, $CH_2OH$, haloalkyl, phenyl, halophenyl or methyl phenoxy;
$R^2$ independently in each occurrence is haloalkyl, phenyl, haloaryl or alkyl;
$R^3$ independently in each occurrence is t-alkyl;
X independently in each occurrence is bromine or chlorine;
a is independently in each occurrence 1 or 2; and
b is independently in each occurrence 0 or 1, with the proviso that at least one $R^1$ is $CH_2OR^3$ or $CH_2OH$.

2. The compounds of claim 1 wherein R is $C_{1-10}$ alkylene or haloalkylene.

3. The compounds of claim 1 wherein $R^1$ is $CH_2OH$, $CH_2OR^3$ or haloalkyl.

4. The compounds of claim 3 wherein $R^1$ is $CH_2OH$ or $CH_2OC(CH_3)$.

5. The compounds of claim 4 wherein $R^1$ is $CH_2OH$.

6. The compounds of claim 3 wherein at least two $R^1$'s are $CH_2OH$ or $CH_2OR^3$.

7. The compounds of claim 6 wherein at least two $R^1$'s are $CH_2OH$.

8. The compounds of claim 1 wherein a is 2 and b is 0.

* * * * *

UNITED STATES PATENT AND TRADEMARK OFFICE
CERTIFICATE OF CORRECTION

PATENT NO. : 4,510,101
DATED : April 9, 1985
INVENTOR(S) : Chester E. Pawloski and Sally P. Ginter It is certified that error appears in the above-identified patent and that said Letters Patent is hereby corrected as shown below:

On title page, second column, approximate line 8, "$(R^2)_p$" should read -- $(R^2)_b$ --.

Column 2, line 28, "$(R^2)_p$" should read -- $(R^2)_b$ --.

Column 5, line 65, the word "group" should read -- group. --

Column 8, line 62, the word "hydroxy" should read -- hydroxyl --.

Column 12, line 13 should read -- 2,2-bis(bromomethyl)-1,3-bis(O,O-di(2-chloro-3-hydroxypropyl)phosphorate) --.

Column 14, line 14, "EXAMPLE 11-20" should read -- EXAMPLES 11-20 --.

Column 15, line 41, "$(R^2)_p$" should read -- $(R^2)_b$ --.

Signed and Sealed this

Seventh Day of January 1986

[SEAL]

Attest:

DONALD J. QUIGG

Attesting Officer    Commissioner of Patents and Trademarks